United States Patent
Kwon et al.

(10) Patent No.: US 12,364,654 B2
(45) Date of Patent: Jul. 22, 2025

(54) METHOD FOR MANUFACTURING SPICULE COATED WITH DIAMOND AND INGREDIENTS EFFECTIVE FOR SKIN IMPROVEMENT, AND DIAMOND SPICULE COSMETIC COMPOSITION INCLUDING THE SAME

(71) Applicant: BN CO., LTD., Anyang-si (KR)

(72) Inventors: Tae Gwang Kwon, Seoul (KR); Moo Seong Jeon, Anyang-si (KR); Hong Bo Shim, Cheongju-si (KR); Hak Ryeol Choi, Yongin-si (KR); Bong Woo Kim, Seoul (KR)

(73) Assignee: BN CO., LTD., Anyang-si (KR)

( * ) Notice: Subject to any disclaimer, the term of this patent is extended or adjusted under 35 U.S.C. 154(b) by 0 days.

(21) Appl. No.: 17/995,174

(22) PCT Filed: Aug. 19, 2022

(86) PCT No.: PCT/KR2022/012376
§ 371 (c)(1),
(2) Date: Sep. 30, 2022

(87) PCT Pub. No.: WO2023/163298
PCT Pub. Date: Aug. 31, 2023

(65) Prior Publication Data
US 2024/0325260 A1    Oct. 3, 2024

(30) Foreign Application Priority Data

Feb. 24, 2022  (KR) ........................ 10-2022-0024357

(51) Int. Cl.
*A61K 8/11* (2006.01)
*A61K 8/58* (2006.01)
*A61K 8/65* (2006.01)
*A61Q 19/08* (2006.01)

(52) U.S. Cl.
CPC ............... *A61K 8/11* (2013.01); *A61K 8/585* (2013.01); *A61K 8/65* (2013.01); *A61Q 19/08* (2013.01); *A61K 2800/28* (2013.01); *A61K 2800/623* (2013.01); *A61K 2800/63* (2013.01)

(58) Field of Classification Search
None
See application file for complete search history.

(56) References Cited

U.S. PATENT DOCUMENTS

2016/0346404 A1* 12/2016 Trogler ................ A61K 9/5192
2021/0196899 A1    7/2021 Song

FOREIGN PATENT DOCUMENTS

| CN | 101626775 A | 1/2010 |
| CN | 107595650 A | 1/2018 |
| KR | 20160064410 A | 6/2016 |
| KR | 101897401 B1 | 9/2018 |
| KR | 102074214 B1 | 2/2020 |
| KR | 102224032 B1 * | 3/2021 |

OTHER PUBLICATIONS

Zhang et al. One-step and high-density protein immobilization on epoxysilane-modified silica nanoparticles. Chinese Sci Bull, 2009, 54:2620-2626 (2009) (Year: 2009).*
Korean Patent Application No. 10-2022-0024357, Office Action dated Apr. 15, 2022, with English translation, eight pages.
Korean Patent Application No. 10-2022-0024357, Notice of Allowance dated May 12, 2022, with English translation, eight pages.
Han et al., "Subjective Skin Improvement and Safety of the Spicules-containing Cosmetics," Journal of Convergence for Information Technology 11(8): 212-223 (2021).

* cited by examiner

*Primary Examiner* — David J Blanchard
*Assistant Examiner* — Sarah J Chickos
(74) *Attorney, Agent, or Firm* — Hoffman Warnick LLC

(57) ABSTRACT

The present disclosure relates to a method for manufacturing a spicule capable of promoting percutaneous absorption of skin improvement active ingredients and fine diamonds, a spicule manufactured thereby, and a cosmetic composition comprising the same. A spicule cosmetic composition prepared according to the present disclosure can be used in the preparation of a cosmetic composition that may have excellent percutaneous penetration efficacy and may be excellent in functionality.

8 Claims, 15 Drawing Sheets

Comparative Example 1  Comparative Example 2

METHOD FOR MANUFACTURING SPICULE COATED WITH DIAMOND AND INGREDIENTS EFFECTIVE FOR SKIN IMPROVEMENT, AND DIAMOND SPICULE COSMETIC COMPOSITION INCLUDING THE SAME

TECHNICAL FIELD

The following description relates to a method for manufacturing an acicular structure for accelerating percutaneous absorption capable of promoting percutaneous absorption of an ingredient effective for skin improvement, an acicular structure manufactured thereby, and a cosmetic composition including the same.

BACKGROUND ART

As appearance is recognized as a measure of health and interest in skin health is heightened accordingly, interest in eco-friendly materials that are harmless to the human body and functionally affect the skin in the cosmetic industry is increasing. Particularly, since synthetic surfactants, pigments, antioxidants, chemical antiseptics, and the like contained in cosmetics are known to have the possibility of making the skin drier, or causing rashes, inflammations, skin diseases, and even skin cancer, there is a high need for cosmetics using natural substances as main ingredients instead of chemical ingredients that are harmful to the skin. Particularly, research on natural-derived functional substances is in the spotlight even in the field of functional cosmetics, which focuses on the incidental functional effects of cosmetics.

Among these natural substances, spicule (spongy bone fragments) is also called sponge. There are 5,000 species or more of sponge as primitive marine organisms without muscles, nerves or organs, and they are living things found regardless of the depth of the sea. Bone fragments are tissues responsible for the function of the needle-shaped skeleton existing in the body of invertebrates, and are composed of silicic acid and calcium carbonate as main ingredients. The fibrous skeleton of sponge has the absorption ability according to capillary phenomenon so that it is being applied in various fields such as medicine. For example, bone fragments of sponge are used for treatment and prevention of diseases by containing antibiotics for the treatment of osteomyelitis.

Since the sponge-derived spicule as described above has an acicular structure, it is particularly suitable for delivering active ingredients up to the percutaneous layer of the skin so that attempts have been made to use it in a cosmetic composition.

As a prior patent document of the present disclosure, Korean Patent No. 10-2074214 and the like exist.

Under this background, the present inventors have completed and provided as an invention an optimal manufacturing method including fine diamond coating and having an amino group modifying step in the use of the sponge-derived acicular structure as described above as a cosmetic composition.

DISCLOSURE OF THE INVENTION

Technical Goals

An aspect provides a method for manufacturing a spicule with excellent percutaneous absorption, and more specifically, a method for manufacturing an acicular structure which contains skin improvement active ingredients and is coated with diamond, and an acicular structure manufactured thereby.

Another aspect provides a cosmetic composition including a spicule manufactured by the method.

However, the technical problems to be achieved by the present disclosure is not limited to the above-mentioned problems, and other problems not mentioned will be clearly understood by those skilled in the art from the following description.

Technical Solutions

According to an aspect, there is provided a method for manufacturing a spicule coated with ingredients effective for skin improvement and diamond, the method including the following steps of:
(a) washing a spicule;
(b) encapsulating a first active ingredient in inner holes of the washed spicule;
(c) coating the outside of the spicule in which the first active ingredient is encapsulated in the inner holes with silica;
(d) coating an amino group by reacting the silica-coated spicule with aminosilane and lysine; and
(e) coating amino group-coated silica with a second active ingredient and diamond.

According to one aspect, aminosilane of the step (d) may be 3-aminopropyltrimethoxysilane.

According to one aspect, lysine of the step (d) may be poly-L-lysine.

According to one aspect, aminosilane and lysine of the step (d) may have a mixing ratio of 1:1 to 500:1.

According to one aspect, diamond of the step (e) may be one or more selected from the group consisting of microdiamonds, nanodiamonds, and colloidal diamonds.

According to one aspect, the first active ingredient and the second active ingredient may each be one or more selected from the group consisting of collagen, fish collagen, nano collagen, low molecular weight collagen, vegetable collagen, collagen peptides, amino acids, tripeptides, tetrapeptides, and water-soluble vitamins, and the first active ingredient and the second active ingredient may be ingredients that are the same as or different from each other.

According to another aspect, there is provided a cosmetic composition including a spicule manufactured by the above-described method.

According to one aspect, the cosmetic composition may have a skin keratin exfoliation effect.

According to one aspect, the cosmetic composition may have a wrinkle improvement effect.

Advantageous Effects

According to the manufacturing method of the present disclosure, a spicule having an excellent degree of amino group modification can be obtained, and thus, percutaneous absorption can be promoted. In addition, the spicule manufactured according to the manufacturing method of the present disclosure may contain a large amount of hydrophilic active ingredients such as collagen in the inner holes, and the outer portion of the spicule is coated with fine diamond to give the excellent skin peeling and skin regeneration effects, and the spicule can also be used in the preparation of a cosmetic composition having excellent

BEST MODE FOR CARRYING OUT THE INVENTION

Figure 1:
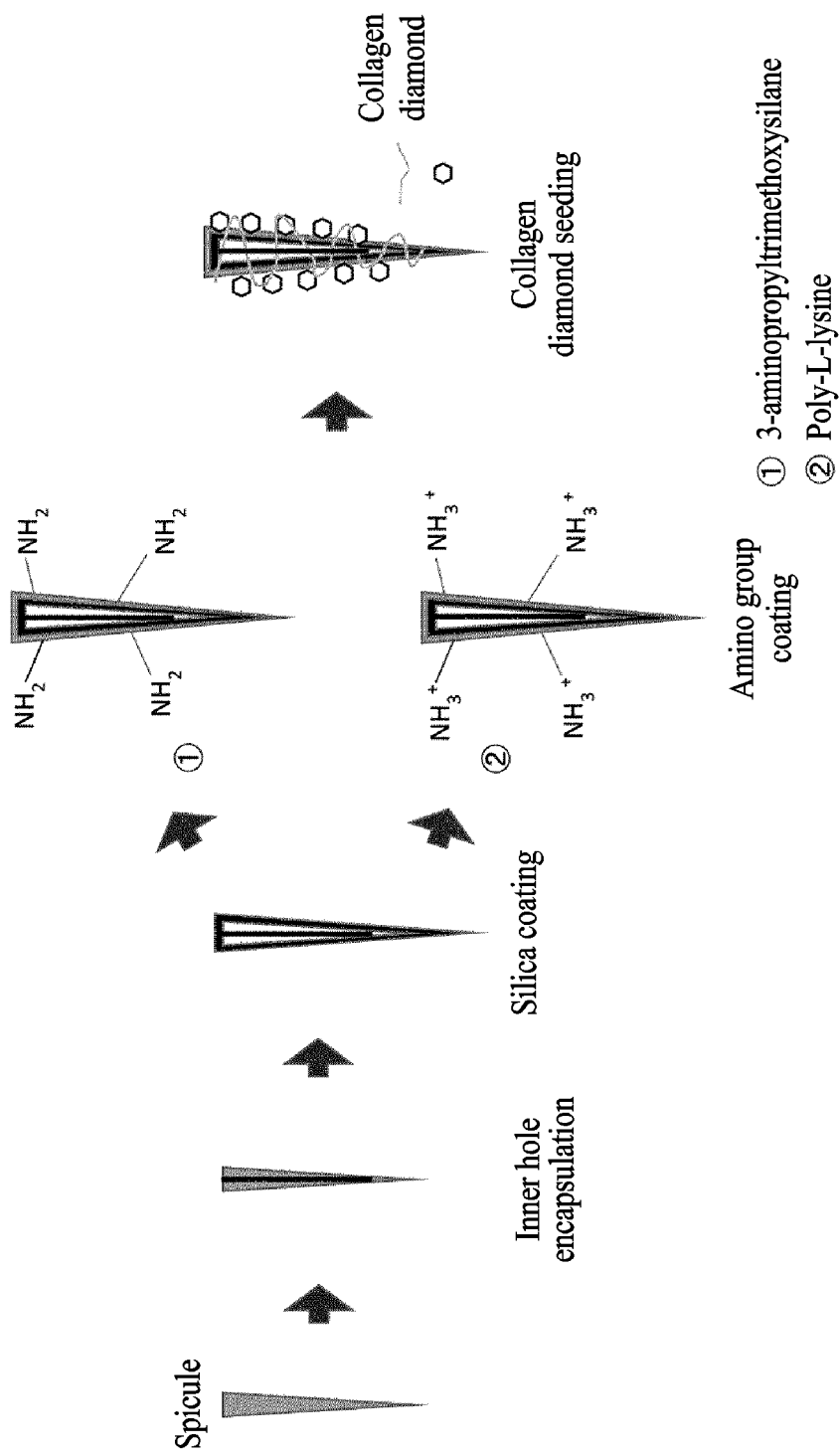
FIG. 1 shows a schematic diagram of a method for manufacturing an acicular structure according to the manufacturing method of the present disclosure.

According to one example of the present disclosure, there is provided a method for manufacturing a spicule containing ingredients effective for skin improvement and diamond, the method including the steps of:

(a) washing a spicule;
(b) encapsulating a first active ingredient in inner holes of the washed spicule;
(c) coating the outside of the spicule in which the first active ingredient is encapsulated in the inner holes with silica;
(d) coating an amino group by reacting the silica-coated spicule with aminosilane and lysine; and
(e) coating amino group-coated silica with a second active ingredient and diamond.

The term used in the present specification, "spicule", "acicular body" or "acicular structure" refers to a structure having an acicular microstructure, and in the present specification, the "spicule", "acicular body" and "acicular structure" may be interchangeably used. Preferably, it may have an acicular structure derived from sponge, and more preferably, the sponge may be *Spongilla lacustris*. The bone fragments or bone 10 needles of the sponge are used as the spicule in the present disclosure.

A spicule may be composed of calcium or silica, and the spicule may have a porous inner portion. The spicule has an I-type structure, a Y-type structure, or an X-type structure. Specifically, the spicule may have a Monoaxon shape, a Triaxon shape, a Tetraxon shape, or a Polyaxon shape. In addition, the Triaxon shape may be a Triactine or Hexactine shape. The "monoaxon" means an acicular spicule with a sharp tip. Preferably, the spicule may have an I-type structure and a monoaxon shape.

The spicule may be one that is obtained from sponge and additionally purified.

The coated spicule may contain ingredients effective for skin improvement therein. A spicule of the present disclosure is characterized in that it includes a pure spicule by removing all natural impurities therein. Therefore, the spicule may contain ingredients effective for skin improvement in the porous structure of the inside thereof.

The ingredients effective for skin improvement may be cosmetically effective ingredients, and may include an ingredient for enhancing or improving skin function, an ingredient for suppressing deterioration of skin condition, an ingredient for supplementing the disadvantages of the skin or highlighting the advantages thereof, or the like. Nonlimiting examples of the active ingredients include collagen, fish collagen, nano collagen, low molecular weight collagen, vegetable collagen, collagen peptides, amino acids, tripeptides, tetrapeptides, water-soluble vitamins, and the like.

The term used in the present specification, "collagen" refers to a semi-crystalline aggregate of collagen molecules. Specifically, collagen is a major protein that forms the extracellular matrix formed in a triple helix composed of amino acids, and is a major ingredient of connective tissue. The collagen may be human body-derived collagen. The human body-derived collagen may be fibrillar collagen or non-fibrillar collagen.

A spicule may be modified by coating the surface thereof. Specifically, the spicule may be one of which the surface is coated with diamond. Such a diamond-coated spicule may improve the skin absorption degree of the active ingredients compared to the spicule that is not coated with diamond so that the skin absorption degree of the active ingredients may be increased.

Diamond used for the coating may be used in a diamond powder or liquid form. At this time, diamond used may be one or more selected from the group consisting of microdiamonds, nanodiamonds and colloidal diamonds. Specifically, diamond may be nanodiamonds.

Further, the spicule may be one including a silica coating on the surface thereof.

Silica coating means one which is coated with a material containing silicon dioxide.

One specific example of silica may be tetraethyl orthosilicate or siloxane polymer. Silica coating may improve the binding performance with the active ingredients by modifying the surface of the acicular body.

The spicule may be one containing an amino group coating on the surface thereof. The amino group coating refers to a coating layer of a material containing an amino group. The amino group coating means coating the spicule surface with a material or amino acid containing an amino group at the terminal thereof.

The amino group coating may be an aminosilane coating and/or a lysine coating.

The term used in the present specification, "amino silane" is an N-silyl compound in which hydrogen is substituted with an amino group, and it is represented by the chemical formula of $SiH_4$, and is also called aminosilane. The amino silane is a kind of a silane coupling agent, and may be one forming a hydrophilic coating layer.

Aminosilane may be N-2-(aminoethyl)-3-aminopropylmethyldimethoxysilane, N-2-(aminoethyl)-3-aminopropyltrimethoxysilane, 3-triethoxysilyl-N-(1,3-dimethylbutylidene) propylamine, N-phenyl-3-aminopropyltrimethoxysilane, N-(vinylbenzyl-2-aminoethyl-3-aminopropyltrimethoxysilane hydrochloride, N-(vinylbenzyl)-2-aminoethyl-3-aminopropyltrimethoxysilane hydrochloride, 3-aminopropyltrimethoxysilane, 3-aminopropyltrimethoxysilane, 3-aminopropyltriethoxysilane, hydrolysates thereof, derivatives thereof, or combinations thereof.

The term used in the present disclosure, "lysine" is a type of amino acid, and may include polylysine, which is a homologous amino acid polymer of lysine. Lysine may be poly-L-lysine, poly-D-lysine, or a combination thereof.

In one embodiment, aminosilane may be 3-aminopropyltrimethoxysilane. In addition, lysine may be poly-L-lysine.

The cleaning of the step (a) is for removing organic impurities present in the inner holes of the acicular body, and may be performed using purified water and a basic or acidic solution. Preferably, cleaning of the acicular body may include the processes of cleaning the acicular body with purified water one or more times and then treating the cleaned acicular body with an acidic solution such as sulfuric acid, hydrochloric acid, hydrofluoric acid, or hydrogen peroxide and a basic solution such as sodium hydroxide or potassium hydroxide.

According to one aspect, the inner hole encapsulation of the step (b) may be performed by ultra-high pressure treatment in which a pressure of 50 to 300 MPa is applied for 1 to 10 minutes, and the first active ingredient may be preferably a hydrophilic active ingredient, and nonlimiting examples thereof include amino acids, tripeptides, tetrapeptides, water-soluble vitamins, and the like. The first active ingredient may be excellently encapsulated in the inner holes under the above conditions.

The coating of silica of the step (c) may be preferably performed by reacting tetraethyl orthosilicate. The silica coating process may improve the binding performance with the active ingredients by modifying the surface of the acicular body. In addition, the coating reaction is preferably performed at 25 to 50° C. for 30 minutes to 2 hours, and may include ultra-high pressure treatment in which a pressure of 50 to 300 MPa is applied for 1 to 10 minutes. The silica coating may be performed to the most excellent degree under the above conditions.

According to one aspect, aminosilane of the step (d) may be 3-aminopropyltrimethoxysilane, and lysine of the step (d) may be poly-L-lysine.

According to one aspect, aminosilane of the step (d) may be one which is contained at a higher weight than lysine. Specifically, aminosilane and lysine may have a weight ratio of 1:1 to 1000:1. Preferably, the weight ratio may be 500:1. Aminosilane is reacted with a spicule in the form of a mixed solution with lysine, and preferably, the mixing ratio may be varied from 0.01 parts by weight to 5 parts by weight based on 1 part by weight of the spicule. If it is out of the above range, there may be a problem in that the encapsulation efficiency of diamond and active ingredients in the spicule is lowered.

As verified in Examples 5 and 6 below, when the mixing weight ratio of aminosilane and lysine was 500:1, the most excellent fluorescent collagen encapsulation ability and skin absorption degree were shown, and particularly, better percutaneous absorption rates could be shown.

The coating of the amino group of the step (d) is a step of modifying the surface of the acicular body, and may be performed preferably after the silica coating. The reaction of coating the amino group may be preferably performed at 25 to 50° C. for 30 minutes to 2 hours, and ultra-high pressure treatment in which a pressure of 50 to 300 MPa is applied for 1 to 10 minutes may be performed. Modification into the amino group may be excellently performed under the above reaction conditions.

According to one aspect, diamond of the step (e) may be one or more selected from the group consisting of microdiamonds, nanodiamonds, and colloidal diamonds.

According to one aspect, the first active ingredient and the second active ingredient may each be one or more selected from the group consisting of collagen, fish collagen, nano collagen, low molecular weight collagen, vegetable collagen, collagen peptides, amino acids, tripeptides, tetrapeptides, and water-soluble vitamins, and the first active ingredient and the second active ingredient may be ingredients that are the same as or different from each other.

According to another aspect, there is provided a cosmetic composition including a spicule manufactured by the above-described method. The content of the spicule is not particularly limited, but may preferably be 0.1 to 5 parts by weight based on 100 parts by weight of the cosmetic composition. The composition can show the most excellent percutaneous absorption rate and skin peeling effect.

The skin improvement active ingredients contained in the cosmetic composition may include an ingredient for enhancing or improving skin function, an ingredient for suppressing deterioration of skin condition, an ingredient for supplementing the disadvantages of the skin or highlighting the advantages thereof, or the like. The content of the active ingredients is not particularly limited, but may preferably be 0.05 to 1 part by weight based on 100 parts by weight of the cosmetic composition. In addition, the cosmetic composition according to the present disclosure may include various ingredients contained in conventional cosmetic compositions in addition to the useful ingredients. For example, it may include all materials commonly used in the mask sheet, such as all dispersants, thickeners, surfactants, antiseptics, humectants, stabilizers, solubilizers, pigments, fragrances, and the like.

According to one aspect, the cosmetic composition may have a skin keratin exfoliation effect.

According to one aspect, the cosmetic composition may have a wrinkle improvement effect.

Such a cosmetic composition according to one example of the present disclosure may further include purified water, antioxidants, stabilizers, pigments, fragrances, or the like commonly used in the field of cosmetic compositions.

Further, the cosmetic composition according to one example of the present disclosure may be prepared in a conventional formulation. Specifically, it may be prepared in a formulation including a cosmetic water (skin lotion), a skin softener, a skin toner, an astringent, a lotion, a milk lotion, a moisture lotion, a nourishing lotion, a massage cream, a nourishing cream, a moisture cream, an eye cream, a hand cream, a foundation, an essence, a nourishing essence, an eye essence, a pack, a soap, a cleansing foam, a cleansing lotion, a cleansing cream, a body lotion, a body cream, a body cleanser, a suspension, a gel, a powder, a paste, a mask pack or sheet, or an aerosol composition. In addition, it can be applied in various properties suitable for providing moisture feeling to the skin, such as a gel or cream phase, a paste phase, a solid phase, and the like, and specifically, it may be a gel cream phase with a feeling of particles such as sorbet or slush. The composition of such a formulation can be prepared according to a conventional method in the art.

In one embodiment, the composition may further include one or more selected from the group consisting of oils, purified water, emulsifiers, dispersants, pigments, fragrances, sunscreens, sweeteners, vitamins, and sequestering agents. In addition, in one embodiment, the composition may further include 0.1% by weight to 3.0% by weight of an antiseptic.

The blending amount of the additional ingredients such as oils can be easily selected by those skilled in the art within a range that does not impair the purpose and effect of the present disclosure.

The cosmetic composition according to one embodiment may preferably be in a cream formulation. For example, when the cosmetic composition has a cream formulation, it may uniformly contain a coated spicule of the present disclosure, and may be not only effective in moisturizing the skin, but also effective in penetrating the spicule into the skin.

The cosmetic composition according to one embodiment may further include additional ingredients commonly used in cosmetics, e.g., any conventional cosmetic ingredients which may be selected from dispersants, thickeners, pigments, fragrances, fillers, preservatives, antiseptics, neutralizers, sunscreens, sweeteners, vitamins, free-radical scavengers, sequestering agents, and mixtures thereof.

Hereinafter, examples will be described in detail with reference to the accompany drawings. However, since various changes may be made to the examples, the scope of rights of the patent application is not restricted or limited by these examples. It should be understood that all modifications, equivalents, and substitutes for the examples are included in the scope of the rights.

The terms used in the examples are used for the purpose of description only, and should not be construed as an intention to limit the present disclosure. The singular expression includes the plural expression unless the context clearly dictates otherwise. In the present specification, it should be understood that a term such as "comprise", "have", or the like is intended to designate that a feature, a number, a step, an operation, a component, a part, or a combination thereof described in the specification exists, but it does not preclude the possibility of existence or addition of one or more other features, numbers, steps, operations, components, parts, or combinations thereof, in advance.

Unless defined otherwise, all terms used herein, including technical or scientific terms, have the same meaning as those commonly understood by those skilled in the art to which the examples belong. Terms such as those defined in a commonly used dictionary should be interpreted as having a meaning consistent with the meaning in the context of the related art, and should not be interpreted in an ideal or excessively formal meaning unless explicitly defined in the present application.

Further, in the description with reference to the accompanying drawings, the same components are assigned the same reference numerals regardless of the reference numerals, and overlapping descriptions thereof will be omitted. In the description of the examples, if it is determined that a detailed description of a related known technology may unnecessarily obscure the gist of the examples, the detailed description thereof will be omitted.

Example 1. Obtaining Spicule

Example 1-1. Cleaning of Spicule

A spicule extracted from *Spongilla lacustris* L. from Russia was used as an acicular structure, and it is a spicule with inner holes formed therein. The spicule with the inner holes formed therein were cleaned through the following process. 100 g of a spicule was put into 1,000 ml of purified water to remove salt, filtered through a 400 mesh polyethylene (PE) filter, and then the spicule left in the filter was washed twice with purified water. After sterilization was performed by putting it into 1,000 ml of 70% ethanol, it was filtered through a 400 mesh polyethylene (PE) filter, and then the spicule left in the filter was washed twice with purified water. Then, the washed spicule was put into a dryer (Hanbaek Science Co., Ltd.) and dried at 50° C.

In order to remove impurities remaining in the dried spicule, the dried spicule was put into 1,000 ml of 35% hydrogen peroxide ($H_2O_2$) (Samchun Chemical Co., Ltd.), and was sonicated at conditions of 300 W and 40 kHz for 1 hour by using an ultrasonic cleaner (Sungdong Ultrasonic Co., Ltd) at 60° C. Then, after filtering the sonicated spicule through a 400 mesh polyethylene (PE) filter, the process of washing the spicule left in the filter with 500 ml of purified water was repeated three times. Thereafter, cleaning of the spicule was completed by passing through the process of putting the washed spicule into a dryer and drying it at 50° C.

Example 1-2. Encapsulation of the First Active Ingredient in the Inner Holes of the Spicule 500 ml of 1N HCL (Sigma-Aldrich) was added to 100 g of the cleaned spicule and reacted for 1 hour, and then 500 ml of 1N NaOH (Sigma-Aldrich) was added thereto, thereby performing neutralization. Thereafter, 1,000 ml of 10% sodium percarbonate was added and reacted for 1 hour to remove organic impurities in the inner holes.

10 g of a mixed solution containing a spicule, and collagen that is a first active ingredient was put into a plastic pack and vacuum-decompressed, and then subjected to pressurization treatment at a pressure of 150 MPa for 5 minutes using an autoclave (Ilshin Autoclave, Suflux®). Then, after filtering the pressurized spicule through a 400 mesh polyethylene (PE) filter, the process of washing the spicule left in the filter with 500 ml of purified water was repeated three times. Thereafter, cleaning of the encapsulated spicule was completed by passing through the process of putting the washed spicule into a dryer and drying it at 50° C.

Example 1-3. Silica Coating

The spicule obtained in Example 1-2 above was reacted in a 1% tetraethyl orthosilicate solution for 1 hour to coat the spicule with silica.

Example 1-4. Amino Group Coating 0.01 parts by weight of 3-aminopropyltrimethoxysilane and 0.01 parts by weight of poly-L-lysine (mixing ratio of 1:1) and 98.98 parts by weight of water were added based on 1 part by weight of the silica-coated spicule obtained in Example 1-3, and reacted for 1 hour to coat the spicule with an amino group. Thereafter, the process of washing the spicule with 500 ml of purified water was repeated 3 times. Thereafter, collagen (Sigma-Aldrich) to which Fluorescein-5-isothiocyanate (FITC) (Thermo Fisher Scientific Inc.) as a fluorescent material was bound and nanodiamonds were added in an amount of 0.01% by weight and reacted at room temperature for 1 hour.

Next, after filtering the prepared mixed solution through a 400 mesh polyethylene (PE) filter, the process of washing a diamond-bonded structure left in the filter with 500 ml of purified water was repeated three times. Thereafter, an acicular structure in which collagen was contained in the inner holes, diamond and fluorescent collagen were bonded to the amino group of the spicule was obtained by passing through the process of putting the washed diamond-bonded structure into a dryer and drying it at 50° C.

Example 2. Preparation Example of Aminosilane to Polylysine Weight Ratio 10:1

The preparation was performed as in Example 1 above except that only the solution composition used for coating the amino group was changed. 0.1 parts by weight of 3-aminopropyltrimethoxysilane and 0.01 parts by weight of poly-L-lysine (mixing ratio of 10:1) and 98.89 parts by weight of water were added based on 1 part by weight of a spicule, and reacted for 1 hour to coat the amino group. All other reaction conditions were the same as in Example 1 except for the solution composition used for the amino group coating.

Example 3. Preparation Example of Aminosilane to Polylysine Weight Ratio 100:1

The preparation was performed as in Example 1 above except that only the solution composition used for coating the amino group was changed. 1 parts by weight of 3-aminopropyltrimethoxysilane and 0.01 parts by weight of poly-L-lysine (mixing ratio of 100:1) and 97.99 parts by weight of water were added based on 1 part by weight of a spicule, and reacted for 1 hour to coat the amino group. All other reaction conditions were the same as in Example 1 except for the solution composition used for the amino group coating.

Example 4. Preparation Example of Aminosilane to Polylysine Weight Ratio 500:1

The preparation was performed as in Example 1 above except that only the solution composition used for coating the amino group was changed. 5 parts by weight of 3-aminopropyltrimethoxysilane and 0.01 parts by weight of poly-L-lysine (mixing ratio of 500:1) and 93.99 parts by weight of water were added based on 1 part by weight of a spicule, and reacted for 1 hour to coat the amino group. All other reaction conditions were the same as in Example 1 except for the solution composition used for the amino group coating.

Comparative Example 1

The process of washing the spicule that had not the first active ingredient encapsulated in the spicule inner holes and did not go through the silica coating and amino group coating processes with 500 ml of purified water was repeated three times. Thereafter, collagen (Sigma-Aldrich) to which Fluorescein-5-isothiocyanate (FITC) (Thermo Fisher Scientific Inc.) as a fluorescent material was bound and nanodiamonds were added in an amount of 0.01% by weight and reacted at room temperature for 1 hour. Next, after filtering the prepared mixed solution through a 400 mesh polyethylene (PE) filter, the process of washing a diamond-bonded structure left in the filter with 500 ml of purified water was repeated three times. Thereafter, an acicular structure having diamond and collagen only on the outer surface of the spicule was obtained by passing through the process of putting the washed diamond-bonded structure into a dryer and drying it at 50° C.

Comparative Example 2

A spicule coated with silica only, obtained through only the processes of Examples 1-1 to 1-3 above was obtained. Then, the process of washing the spicule with 500 ml of purified water was repeated 3 times. Thereafter, collagen (Sigma-Aldrich) to which FITC as a fluorescent material was bound and nanodiamonds were added in an amount of 0.01% by weight and reacted at room temperature for 1 hour. Next, after filtering the prepared mixed solution through a 400 mesh polyethylene (PE) filter, the process of washing a diamond-bonded structure left in the filter with 500 ml of purified water was repeated three times. Thereafter, a structure in which diamond and fluorescent collagen were bonded to the amino group of the spicule was obtained by passing through the process of putting the washed diamond-bonded structure into a dryer and drying it at 50° C. The amino group coating was not performed in this acicular structure.

Comparative Example 3

0.01 parts by weight of a 3-aminopropyltrimethoxysilane solution and 99.9 parts by weight of water were added to 1 part by weight of the spicule coated with silica only, obtained through only the processes of Examples 1-1 to 1-3 above, and reacted for 1 hour to coat the amino group. Then, the process of washing the spicule with 500 ml of purified water was repeated 3 times. Thereafter, collagen (Sigma-Aldrich) to which FITC as a fluorescent material was bound and nanodiamonds were added in an amount of 0.01% by weight and reacted at room temperature for 1 hour. Next, after filtering the prepared mixed solution through a 400 mesh polyethylene (PE) filter, the process of washing a diamond-bonded structure left in the filter with 500 ml of purified water was repeated three times. Thereafter, a structure in which diamond and fluorescent collagen were bonded to the amino group of the spicule was obtained by passing through the process of putting the washed diamond-bonded structure into a dryer and drying it at 50° C. Poly-L-lysine was not used in the amino group coating of this acicular structure.

Table 1 below summarizes spicule manufacturing conditions of Comparative Examples and Examples above and the fusion rate results of diamond and collagen outside the spicule structures obtained as results of the spicule manufacturing conditions. The following diamond collagen fusion rate (%) was calculated as follows.

$$\text{Fusion rate (\%)} = (\text{fluorescence value of collagen bound to the spicule after fusion of diamond and collagen})/\text{fluorescence value of total collagen used}) \times 100$$

TABLE 1

| Conditions | Spicule inner hole encapsulation | Silica coating of spicule | Coating of 3-aminopropyltrimethoxy silane to poly-L-lysine | Fusion rate of diamond and collagen (%) |
|---|---|---|---|---|
| Comparative Example 1 | x | x | x | 0.2 |
| Comparative Example 2 | o | o | x | 0.2 |
| Comparative Example 3 | o | o | x | 0.6 |
| Comparative Example 4 | o | o | 1:0 | 0.5 |
| Example 1 | o | o | 1:1 | 1.7 |
| Example 2 | o | o | 10:1 | 6.8 |
| Example 3 | o | o | 100:1 | 15.7 |
| Example 4 | o | o | 500:1 | 52 |

Referring to Table 1, it can be seen that the fusion rates of diamond and collagen of Examples of the present disclosure are excellent.

Experimental Example 1. Inner Hole Encapsulation Evaluation

Figure 2:
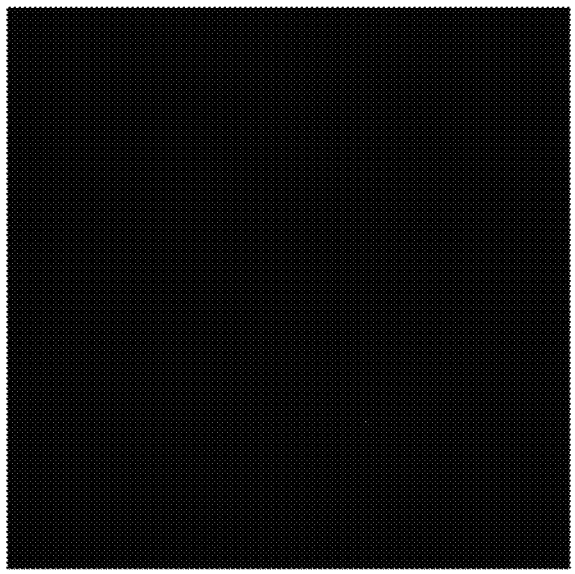
FIG. 2 shows the degrees of fluorescence color development of fluorescent collagen according to whether it is encapsulated in the inner holes or not.
Figure 2:
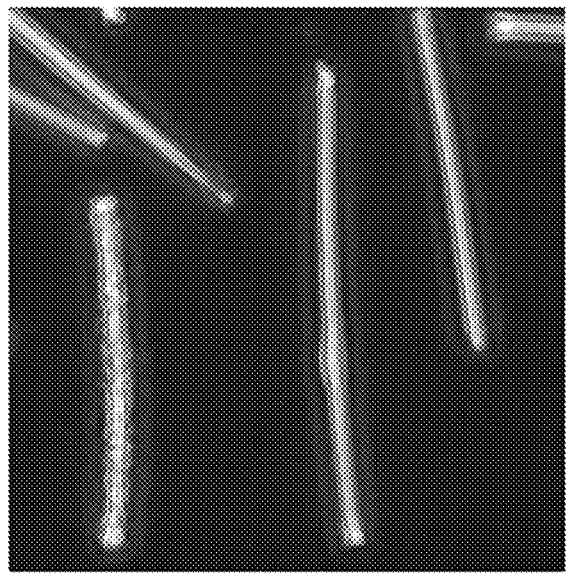

For the evaluation of inner hole encapsulation, the spicule of Comparative Example 1 in which inner hole encapsulation was not performed and the spicule of Comparative Example 2 in which inner hole encapsulation was performed were selected and evaluated. After 5 mg of a spicule and 1 mg of FITC were put and mixed in 0.2 ml of purified water to prepare a mixed solution, 0.1 mg of the spicule was taken from the prepared mixed solution, placed on a slide glass, and observed with a fluorescence microscope (Nikon, Ts2-FL) GFP filter. The results are shown in FIG. 2. As shown in FIG. 2, the spicule of Comparative Example 2 in which inner hole encapsulation was performed exhibited superior fluorescence compared to the spicule of Comparative Example 1 in which inner hole encapsulation was not performed. That is, it was confirmed that the active ingredients could be impregnated into the spicule through the inner hole encapsulation of the spicule.

Experimental Example 2. Fluorescent Collagen Encapsulation Evaluation

Figure 3:
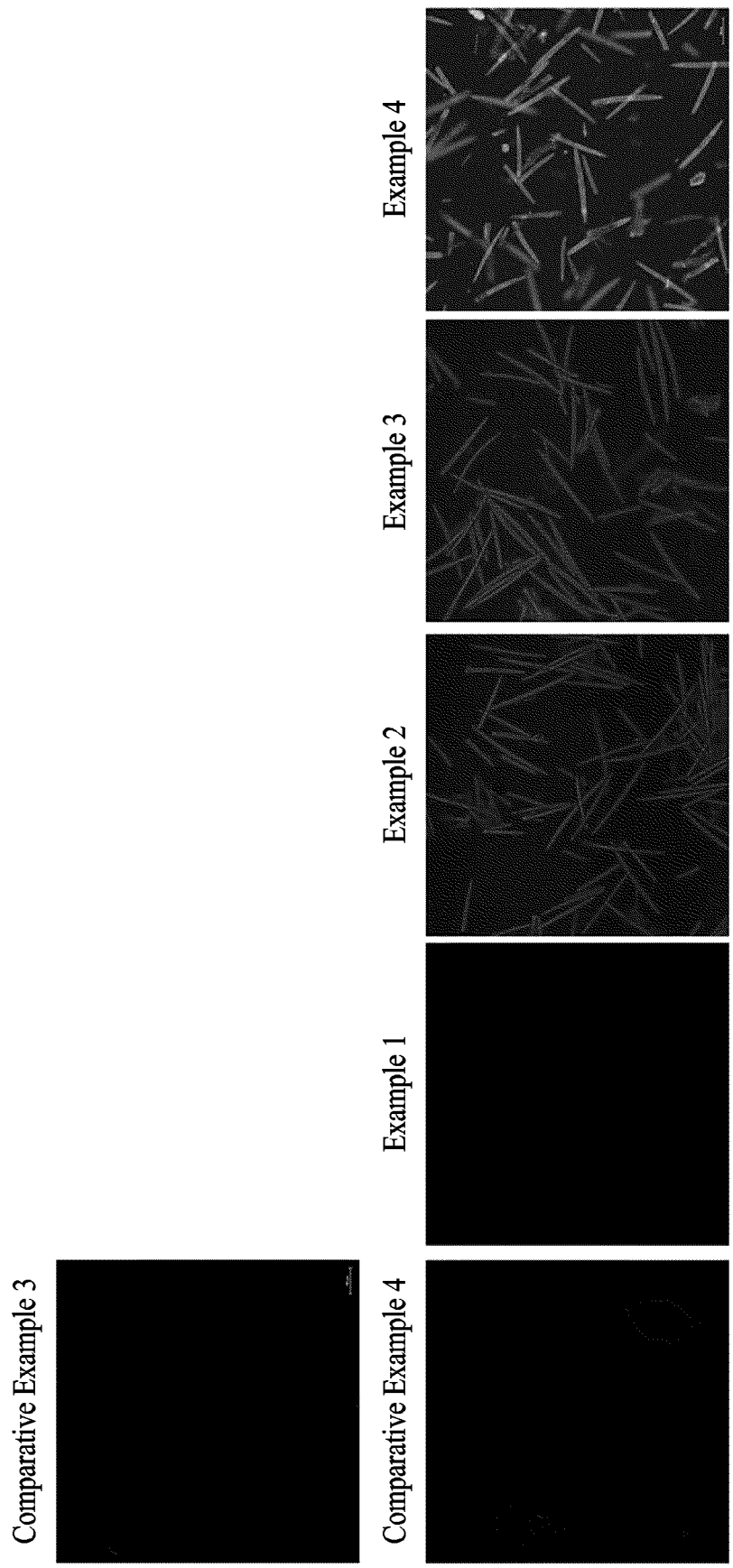
FIG. 3 shows the degrees of fluorescence color development of Preparation Examples prepared by using different manufacturing methods.

For the evaluation of the fluorescent collagen encapsulation ability of the spicules, the spicules obtained in Comparative Examples 3 and 4 and Examples 1 to 4 were evaluated as follows. After 5 mg of a spicule was put into 0.2 ml of purified water and mixed to prepare a mixed solution, 0.1 mg of the spicule was taken from the prepared mixed solution, placed on a slide glass, and observed with a fluorescence microscope (Nikon, Ts2-FL) GFP filter. The results are shown in FIG. 3. As shown in FIG. 3, it could be confirmed that the encapsulation of fluorescent collagen was excellently performed in Example 4.

Experimental Example 3. Preparation and Functionality Evaluation of Cosmetic Compositions 3-1. Cosmetic Composition Preparation Cosmetic compositions were prepared using the spicules of Comparative Example 2 and Examples 1 to 4 of Table 1 above. Specifically, 10.0% by weight of glycerin (humectant), 3.0% by weight of butylene glycol, 1.0% by weight of sodium chloride, and 4.0% by weight of hydrolyzed collagen were put into 59.675% by weight of purified water and stirred at 1,000 rpm for 10 minutes to prepare a water-phase dissolved material. Thereafter, in order to prepare an oil-phase dissolved material, 8.0% by weight of caprylic/capric triglyceride (oil), 4.0% by weight of diisostearylmalate (oil), 4.0% by weight of cetyl PEG/PPG-10/1 dimethicone (emulsifier), and 3.0% by weight of butylene glycol dicaprylate/dicaprate were mixed and dissolved by heating at 60° C., and the prepared water-phase dissolved material was put and stirred at 1,000 rpm to prepare the oil-phase dissolved material. Thereafter, 2% by weight of the spicules (Comparative Examples 3 and 4 and Examples 1 to 4 respectively) based on the total weight of the cosmetic composition was additionally put and stirred at 2,000 rpm and 60° C. for 5 minutes. Finally, a cosmetic composition was prepared by passing through the process of putting 0.025% by weight of a diamond powder, 1.0% by weight of a preservative, and 0.3% by weight of a fragrance, and performing stirring at 3,000 rpm and 50° C. for 5 minutes. Hereinafter, the cosmetic compositions obtained by blending the spicules of Comparative Examples 3 and 4 above are referred to as Compositions 1 and 2 respectively, and the cosmetic compositions obtained by blending the spicule of Example 4 above are referred to as Composition 3 respectively.

3-2. Evaluation of Skin Absorption Degrees of Cosmetic Compositions

Figure 4:
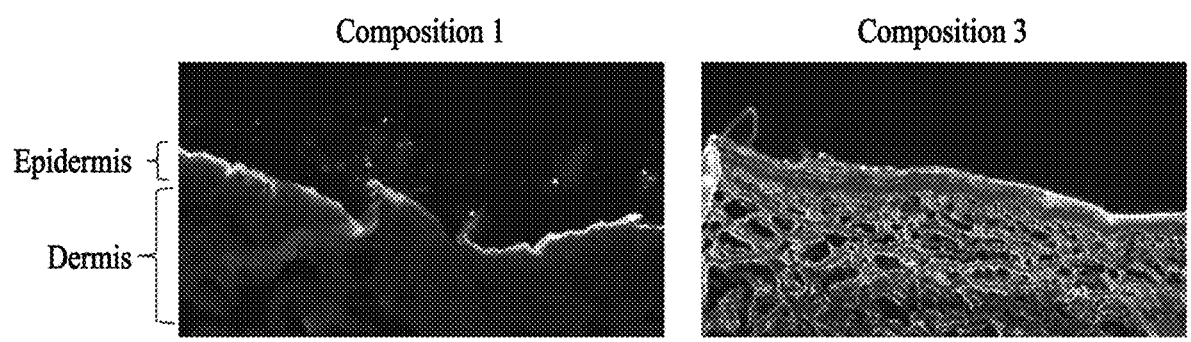
FIG. 4 shows the skin absorption degrees of the cosmetic composition prepared by including the acicular structure of the Preparation Example.

An experiment was conducted to check the degree of skin absorption (penetration) for Compositions 1 to 3 obtained in 3-1 above. The tissue sections of pig skin obtained through the process of applying each of the Compositions 1 to 3 to pig skin (Franz Cell Membrane, FCM, APURES) were observed with a fluorescence microscope (Nikon, Ts2-FL), and the results are shown in FIG. 4 and Table 2. At this time, the tissue sections were obtained by repeating the process of spreading 0.25 g of the composition on pig skin (2×2 cm) and applying it thereto 4 times at 10-minute intervals, left it at room temperature for 24 hours, and then putting it into 2 ml of 3.7% formaldehyde (Sigma-Aldrich) for 20 minutes to immobilize it, washing it 3 times with 1×PBS, putting it into an optimal cutting temperature compound (OCT, Sakura Finetek) to freeze it at −20° C., and cutting it to a thickness of 15 µm by cryostat microtome (Leica Biosystems).

TABLE 2

| Classification | Composition 1 | Composition 2 | Composition 3 |
|---|---|---|---|
| Skin permeability (%) | 0.2 | 0.5 | 22.3 |

Referring to FIG. 4 and Table 2, it could be confirmed that fluorescence was not observed from the percutaneous and dermal layer of the skin in Compositions 1 and 2, whereas fluorescence was observed from the epidermis and dermal layer of the skin in Composition 3. This is because the fluorescent protein has penetrated to the epidermis and dermis layer. It supports that the cosmetic composition according to the present disclosure has a very excellent skin absorption (penetration) degree.

3-3. Skin Peeling Evaluation

Figure 5:
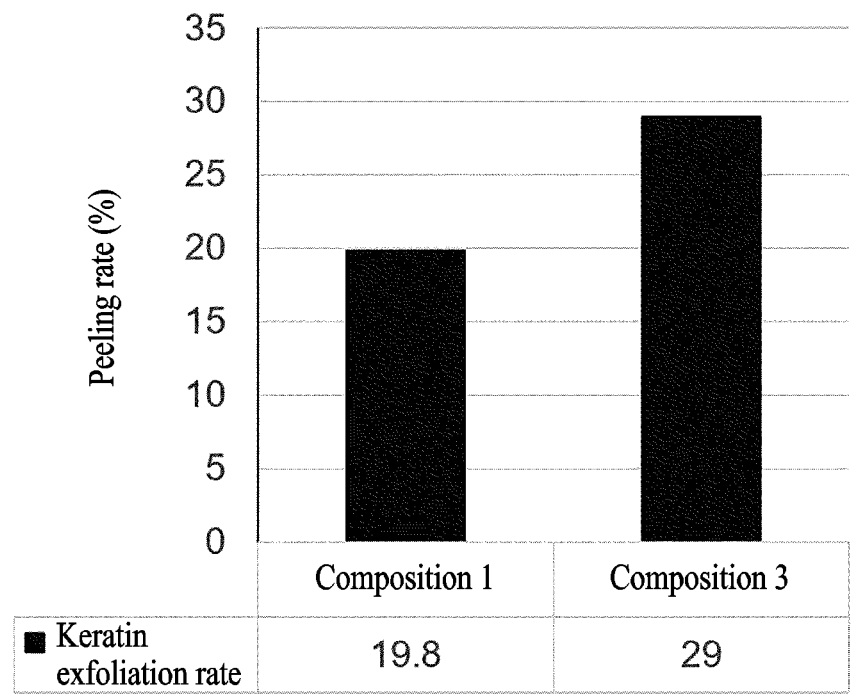
FIG. 5 is an evaluation of the skin peeling effect of the cosmetic composition including the acicular structure according to the manufacturing method of the present disclosure.

In order to check the skin keratin exfoliation degree of the cosmetic compositions of Composition 1 and Composition 3, the keratin exfoliation effects were measured on 15 adult males and females aged 20 to 40 years, and the results are shown in FIG. 5. Specifically, the test subjects put 10% by weight of dihydroxy acetone in the heel top chamber before applying the sample and attached it to the inside of the upper arm for 5 hours. After 24 hours, the color of the colored area was measured with a chromameter (Minolta) to measure the difference in color between before and after application of the sample. An appropriate amount of the cosmetic compositions of Composition 1 and Composition 3 was taken and applied to the affected area twice each morning and afternoon for 2 weeks. Thereafter, the degree of decoloration was measured with a chromameter to measure the time it takes to return to the original skin color. The keratin exfoliation rate was calculated by the formula below.

Keratin exfoliation rate (%) =

(Turnover time of blank −

Turnover time when sample is applied)/(Turnover time of blank) * 100

Turnover time of blank: The time it takes for the stratum corneum of the untreated sample group to be replaced with a new stratum corneum Turnover time when sample is applied: The time it takes for the stratum corneum of the treated sample group to be replaced with a new stratum corneum As shown in FIG. 5, the group treated with Composition 3 exhibited an excellent keratin exfoliation rate.

3-4. Evaluation of Improvement of Wrinkles Around the Eyes

Figure 6:
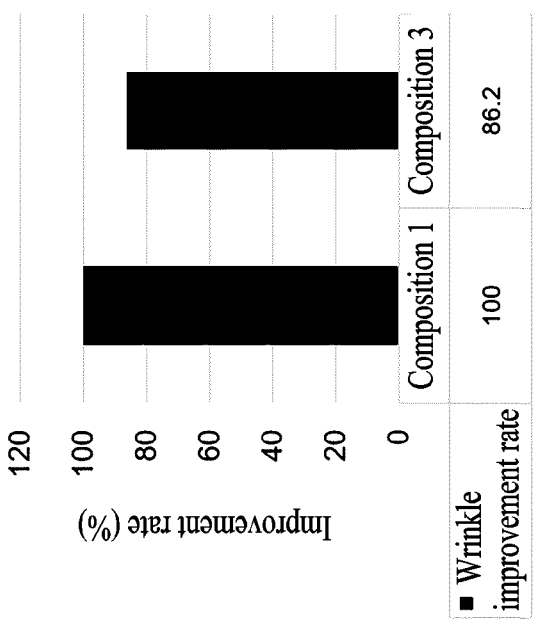
FIG. 6 is an evaluation of the eye wrinkle improvement effect of the cosmetic composition including the acicular structure according to the manufacturing method of the present disclosure.
Figure 6:
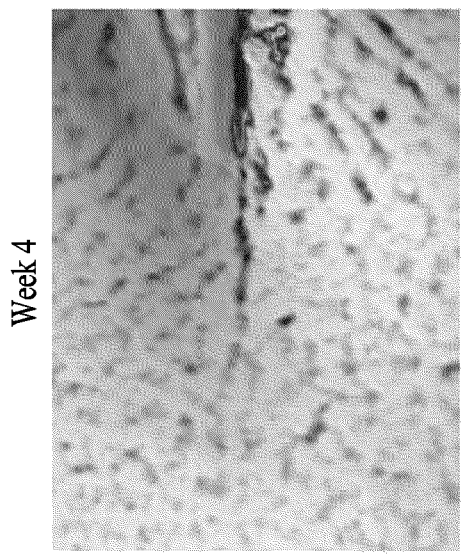
Figure 6:
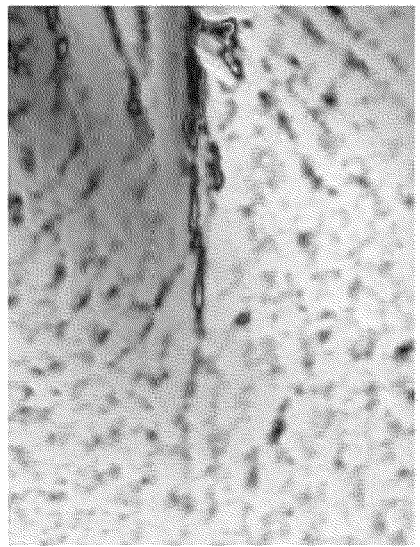

In order to check the anti-skin aging effect of Composition 3, it was evaluated whether or not wrinkles around the eyes were improved based on the standard operating procedures (SOP) of the Cosmetics Clinical Research Support Center of Semyung University, and the results are shown in FIG. 6. Specifically, 20 female test subjects aged to 55 years (average age 42.9 years) took an appropriate amount of the cosmetic composition of Composition 3 twice daily for 4 weeks in the morning and afternoon and 20 applied it around the eyes. Thereafter, in order to analyze wrinkles around the eyes, after 2 weeks and 4 weeks under constant temperature and humidity (22±2° C., RH40 to 60%) conditions, the subjects eye areas were imaged with Antera 3D (Miravex, Ireland), and then instrumental analysis values were measured using an analysis program (Antera 3D software, Miravex, Ireland) provided by the instrument. The picture on the left of FIG. 6 is a photograph taken of the same site at weeks 0 and 4, and the graph on the right shows the reduction rate of wrinkles around the eyes. According as the cosmetic composition of Composition 3 is used, it could be confirmed that the wrinkles around the eyes were improved by 13.8% at the 4th week compared to the 0th week.

Experimental Example 4. Confirmation of In Vitro Collagen Production Effect of Cosmetic Composition 4-1. Experimental Materials and Preparation The in vitro collagen production effect was confirmed using the ivory cream formulation of Composition 3 above.

Fetal bovine serum (FBS), r-Human Fibroblast Growth Factor-B (rhFGF-B), INSULIN, Gentamicin sulfate, Amphotericin-(GA1000) Fibroblast Basal Medium (FBM) used in cell experiments were purchased from Lonza (USA), and EZcytox was purchased from Daeil Lab Service Co., Ltd. (Korea) and used. Particularly, a culture medium having a final concentration of 0.001%, 0.005%, and 0.010% (hereinafter "each experimental group") of the cosmetic composition was prepared in the test for measuring intracellular collagen production. The following experiments were conducted at the PNK Skin Clinical Research Center.

4-2. Cell Line Selection and Cell Culture

Normal Human Dermal Fibroblasts (NHDF) cells, a human fibroblast cell line, were purchased from Lonza and cultured in a 37° C., 5% $CO_2$ thermostat using an FBM medium containing 0.1% INSULIN, 0.1% rhFGF-B, 0.1% GA-1000, and 2% fetal bovine serum (FBS), and subculture was performed once every 2 to 3 days.

4-3. Cell Viability Assessment

The cultured NHDF cells were inoculated in a 24-well plate at a concentration of $2.0 \times 10^4$ cells/well and cultured for 24 hours, and then cultured for 24 hours after the medium of each experimental group was exchanged with serum-free FBM. After performing culturing, 50 µl of EZ-Cytox was added per well and further cultured for an hour. The cultured medium was transferred to a 96-well plate and absorption degree was measured at 450 nm using a VERSA max microplate reader (Molecular devices, LCC, USA). The average absorption degree value for each sample group was obtained, and the cell viability was investigated by comparing it with the absorption degree value of Composition 1 as a control group.

Figure 7:
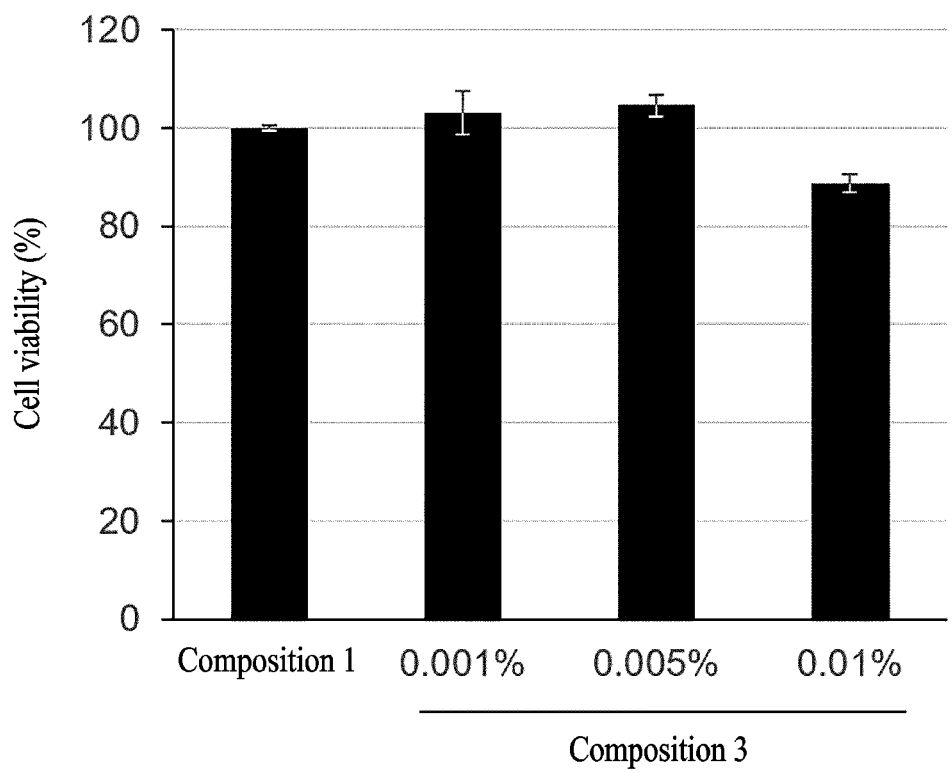
FIG. 7 is a graph showing the cell survival effect of the cosmetic composition including the modified spicule of the present disclosure.

As a result, as shown in FIG. 7, it was confirmed that the cosmetic composition according to the present disclosure had no cytotoxicity compared to Composition 1 as a control group.

4-4. Quantification of Collagen Production Amount

The NHDF cells were inoculated in a 24-well plate at a concentration of $2.0\times10^4$ cells/well and cultured for 24 hours, and then cultured for 24 hours after exchanging the medium of each experimental group with serum-free FBM. After performing culturing for 24 hours, the supernatant was taken and the amount of procollagen released in the medium was measured by using the Procollagen Type I C-peptide (PIP) EIA Kit. Absorption degree was measured at 450 nm using a VERSA max microplate reader (Molecular devices, LCC, USA).

Figure 8:
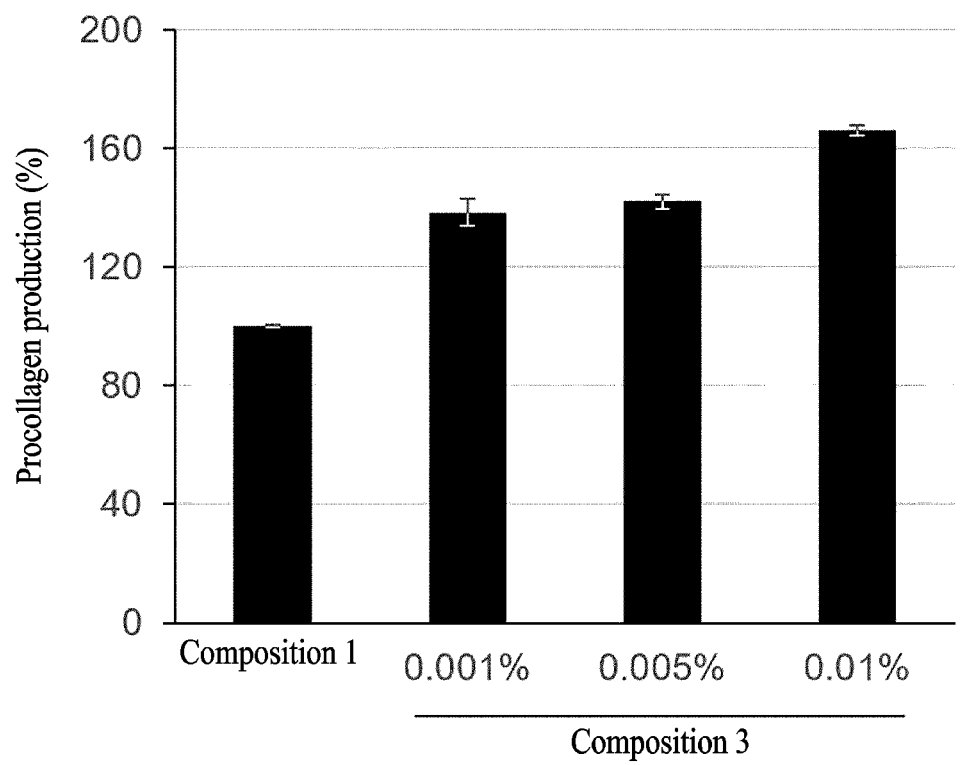
FIG. 8 is a graph showing the collagen synthesis effect of the cosmetic composition including the modified spicule of the present disclosure in NHDF cells.

As a result, as shown in FIG. 8, the cosmetic composition according to the present disclosure significantly increased intracellular collagen (PIP) production amount in a concentration-dependent manner. Specifically, the production amount of intracellular collagen (PIP) was significantly increased to 138.52% to 166.20% in a concentration-dependent manner in the cosmetic composition at a concentration of 0.001% to 0.010%.

4-5. Measurement of Fluorescence Image of Collagen Fiber Production

After the NHDF cells were inoculated in a 24-well plate at a concentration of $2.0\times10^4$ cells/well and cultured for 24 hours, and then cultured for 24 hours after exchanging the cultured NHDF cells with serum-free FBM containing samples diluted for each concentration. After 24 hours of culturing, HEPES-BSS was washed, and then intracellular collagen fibers were stained according to the immunofluorescence staining method. Thereafter, the degree of fluorescence expression was measured using a fluorescence microscope. All of the above results were indicated as mean±standard deviation, and the indicated experimental results are the results of three or more independent experiments, and statistical significance was verified at a significance level of $p<0.05$ by an independent t-test.

Figure 9:
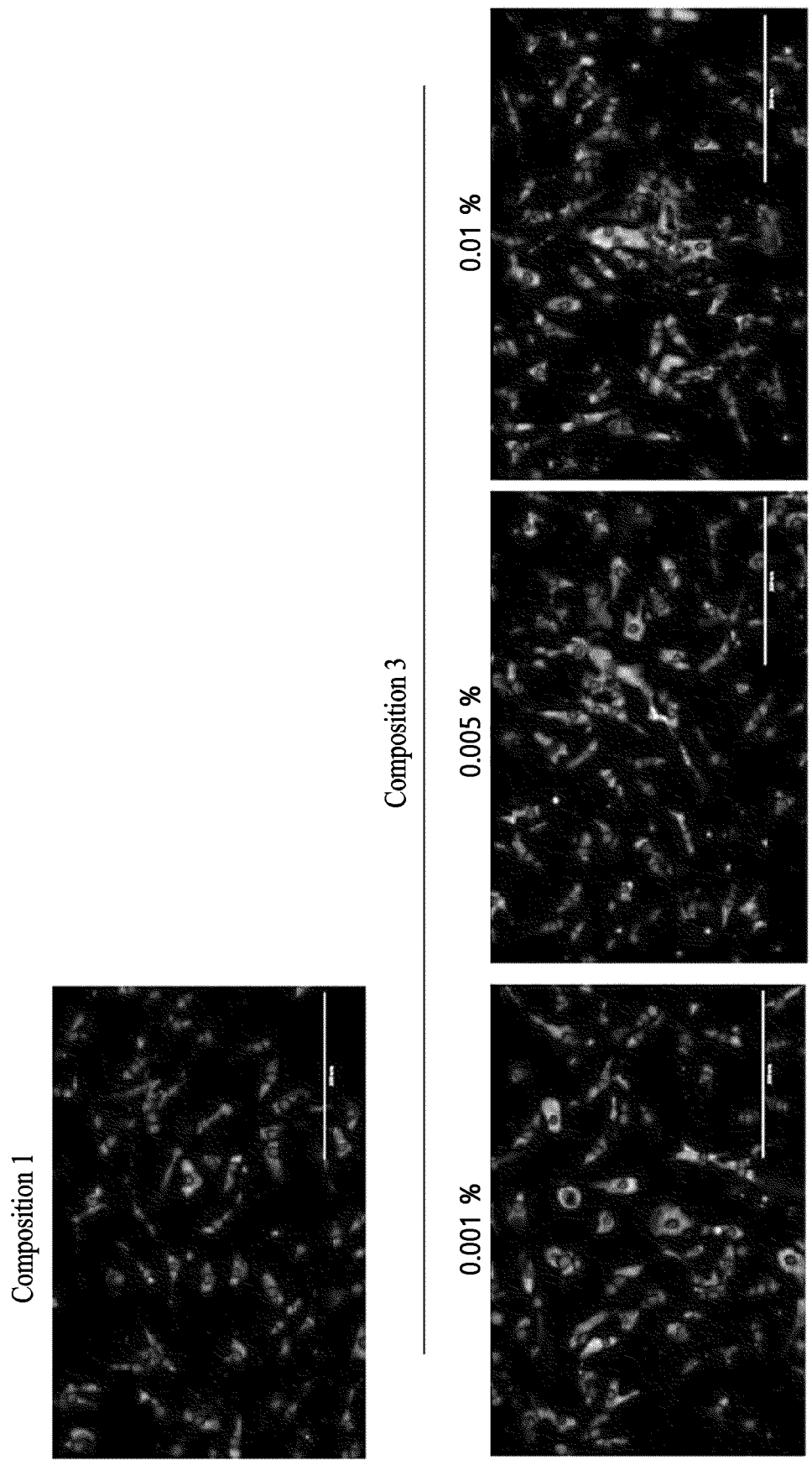
FIG. 9 is photographs showing the effects of the cosmetic composition including the modified spicule of the present disclosure on collagen fiber production in NHDF cells (green: collagen fiber, scale bar: 20 μm).

As a result, as shown in FIG. 9, when the cosmetic composition according to the present disclosure was treated, it was confirmed that the degree of collagen fiber production was increased at all concentrations.

Experimental Example 5. Confirmation of Skin Absorption Degree of the Cosmetic Composition 5-1. Selection of Test Subjects As shown in Table 3 below, twenty one adult women (iv) who may be followed up during the test period and (v) who are aged 20 to 59 years were selected as people who have no exclusion conditions, (i) who have wrinkles around the eyes, nasolabial folds, forehead wrinkles, neck wrinkles, and glabellar wrinkles, (ii) who have voluntarily written and signed the consent form after listening to enough explanations about the matters to be informed to the test subject from a person in charge of test or a person delegated by the person in charge of test, and (iii) who are healthy persons without infectious skin diseases and chronic physical diseases.

TABLE 3

| Full age (years) | Number of people (persons) | % |
|---|---|---|
| 20-29 | 0 | 0.000 |
| 30-39 | 0 | 0.000 |

TABLE 3-continued

| Full age (years) | Number of people (persons) | % |
|---|---|---|
| 40-49 | 11 | 52.381 |
| 50-59 | 10 | 47.619 |

The average age of the twenty one test subjects was 48.762 years old, consisting of 11 people in their 40s and 10 people in their 50s. In addition, the skin conditions of the twenty one test subjects were 14 dry skin, 4 medium dry skin, and 3 neutral skin.

Further, in the questionnaire about skin diseases, itchiness, stinging, erythema, cosmetic side effects, drug side effects, photosensitivity, and atopic disease experiences for each test subject, no test subjects were eligible, and no test subjects had experience with other items.

After explanation of the test, measurements were performed as shown in Table 4 below for the test subjects who agreed to participate in the test and signed the consent form. After using the product, skin symptom evaluation was performed. After the end of the test, the validity and preference surveys were conducted.

TABLE 4

| | Measurement point Visit 1 | |
|---|---|---|
| Measurement item | Before using | After 30 minutes of using |
| subject consent form | O | — |
| Demographic survey | O | — |
| Review of selection/ exclusion criteria | O | — |
| Medical history survey | O | — |
| Concomitant drug | O | — |
| Health status survey | O | — |
| Skin absorption degree | O | O |
| Adverse reactions (safety evaluation) | (O) | O |
| Survey | — | O |

5-2. Measurement Method

For the instrumental evaluation, the test subjects were allowed to adjust the skin surface temperature and humidity to the environment of the measurement space by taking a rest for 30 minutes in a waiting room under constant temperature and humidity conditions with an indoor temperature of 20° C. to 24° C. and a humidity of 40 to 60%. While they taking a rest, water intake was limited. For objective measurement, one researcher performed measurement, and the same area was measured at every measurement.

5-3. Checking Skin Absorption Degree, Absorption Depth, and Absorption Speed

Skin absorption degree was measured using a 3D Raman Microscopy System Nanofinder®30 (TOKYO INSTRUMENTS, Japan).

Particularly, the 3D Raman system used in the test is equipment fabricated to enable fine spacing to be adjusted in the x, y, and z directions, and the z-axis focal length can be moved from the skin surface to the inside of the skin in micrometer units. Therefore, it is possible to obtain a three-dimensional Raman spectrum image according to depth without damaging the skin of the test subject, and when this is used, it is possible to determine the skin absorption degree of cosmetics.

After dividing two regions of the 3×4 cm² test/control site on the left forearm of the test subject, three-dimensional Raman scanning was carried out in a state that the forearm was fixed to the equipment, and measurements were made before using and after 30 minutes of using the product respectively. The laser used for the measurement was 785 nm and the scanning step was fixed at 5 μm. Since it was set to take 5 points in the x- and y-axis directions and 11 points in the z-axis direction, the skin absorption degree of cosmetics can be known from the skin surface to a depth of 50 μm. In addition, this can be converted into absorption depth (μm) and absorption speed (μm/h).

Skin absorption degree was evaluated in a total of 10 steps by dividing the z-axis into 10 equal parts at intervals of 5 μm on the second dimensional image. Therefore, the skin absorption depth can be converted by multiplying the change in skin absorption degree between before using the product and after 30 minutes of using the product by 5 μm, and the skin absorption speed can be converted by dividing the absorption depth by 0.5 hour that is the use time.

Figure 10:
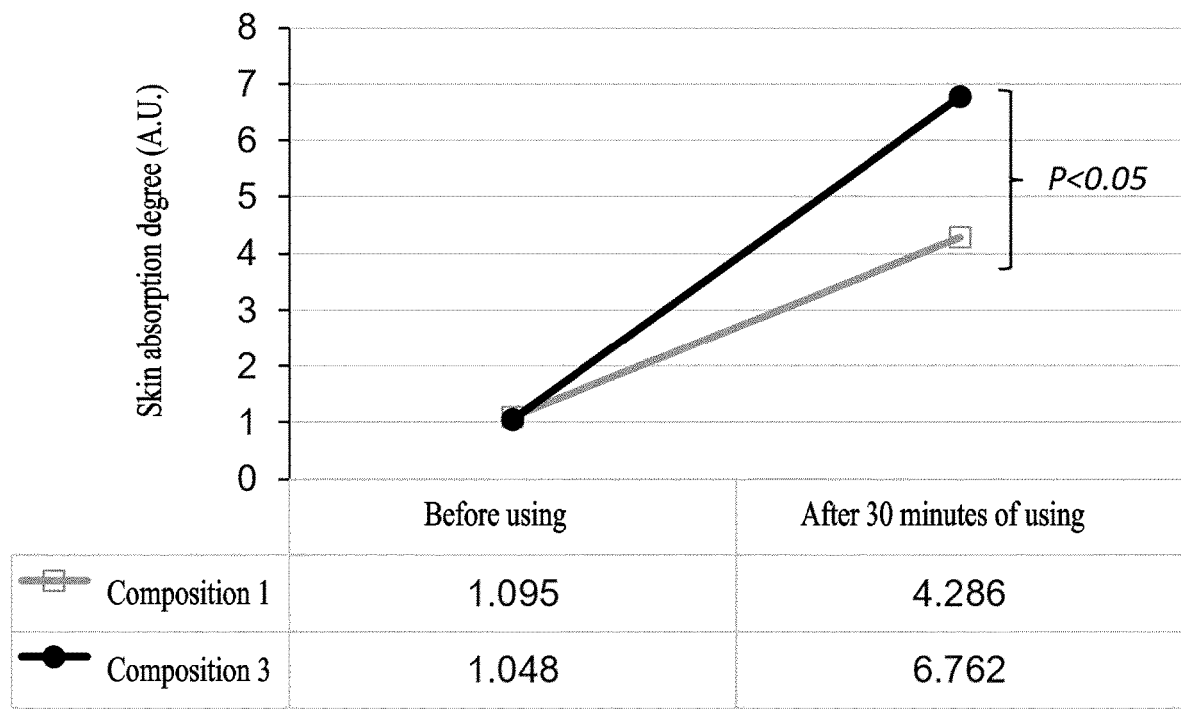
FIG. 10 is a graph showing the skin absorption degrees of the cosmetic composition 3 including the modified spicule of the present disclosure and Cosmetic Composition 1 including a general spicule.
Figure 11:
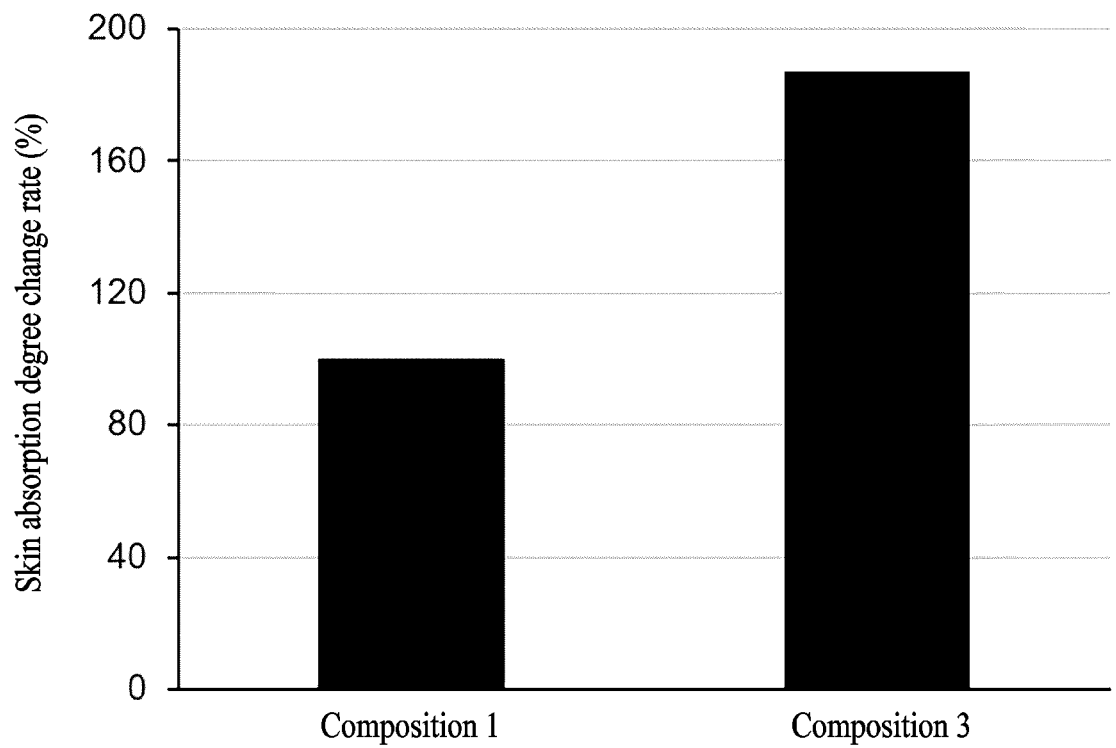
FIG. 11 is a graph comparing the skin absorption degrees of the cosmetic composition 3 including the modified spicule of the present disclosure and Cosmetic Composition 1 including a spicule that is not coated with diamond.

As shown in Table 5, and FIGS. 10 and 11, the skin absorption degree was statistically significantly improved after 30 minutes of using by using Composition 3 according to the present disclosure compared with before using.

Further, it was confirmed that Composition 3 showed remarkable 1.871 times and 187% effects compared to Composition 1, which is a control group including the spicule that is not coated with diamond, and a statistically significant difference appeared even after 30 minutes of using. These results mean that the cosmetic composition according to the present disclosure that is coated with diamond has a remarkable skin absorption effect than the control group that is not.

TABLE 5

| | (Mean ± SD) | | |
|---|---|---|---|
| | | A.U. | |
| Classification | | Composition 3 | Composition 1 |
| Before using | | 1.048 ± 0.218 | 1.095 ± 0.301 |
| After 30 minutes of using | | 6.762 ± 2.587 | 4.286 ± 2.148 |
| Improvement rate (%) | Before using-After 30 minutes of using | 545.229 | 291.416 |
| Ratio (%) of improvement rate (%) of Composition 3/ Composition 1 | Before using-After 30 minutes of using | 187.097 | 100.000 |
| Intragroup p-value comparison | Before using-After 30 minutes of using | 0.000# | 0.000# |
| Intergroup p-value comparison | Composition 3-Composition 1 | 0.000FF | |

Figure 12:
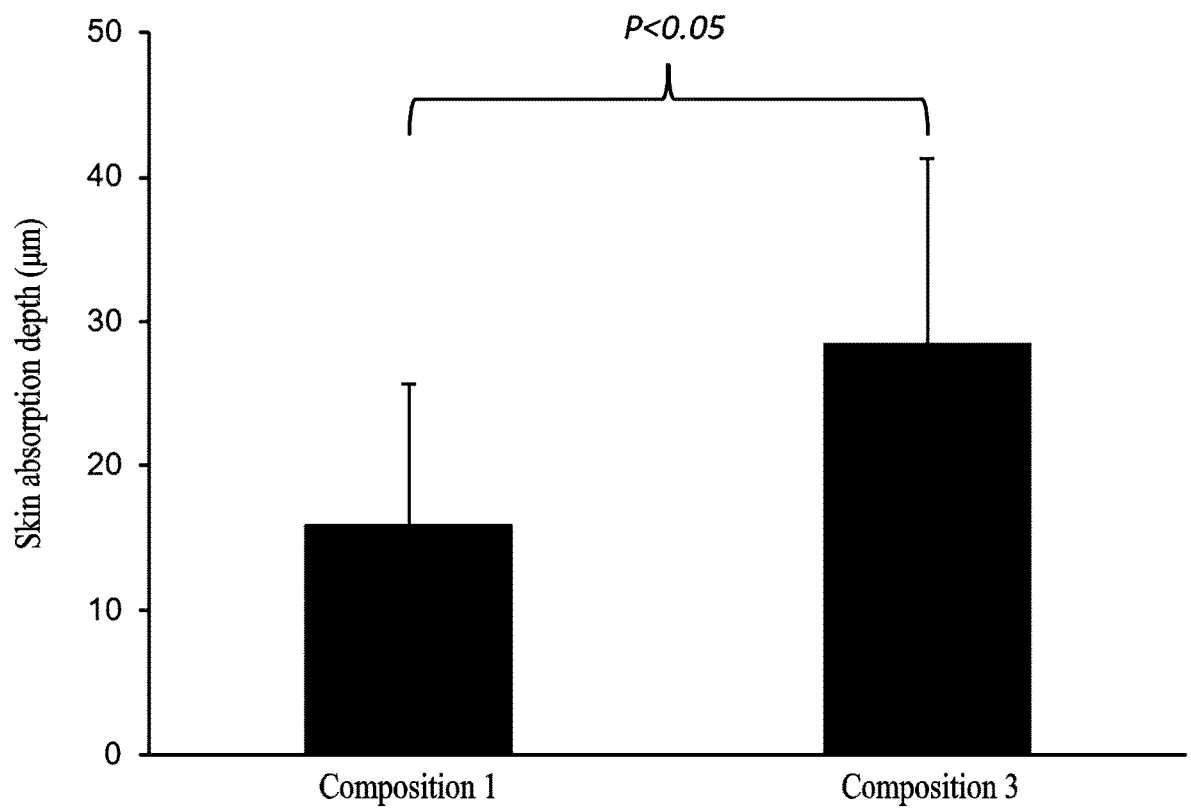
FIG. 12 is a graph showing the skin absorption depths of the cosmetic composition 3 including the modified spicule of the present disclosure and Cosmetic Composition 1 including a spicule that is not coated with diamond.
Figure 13:
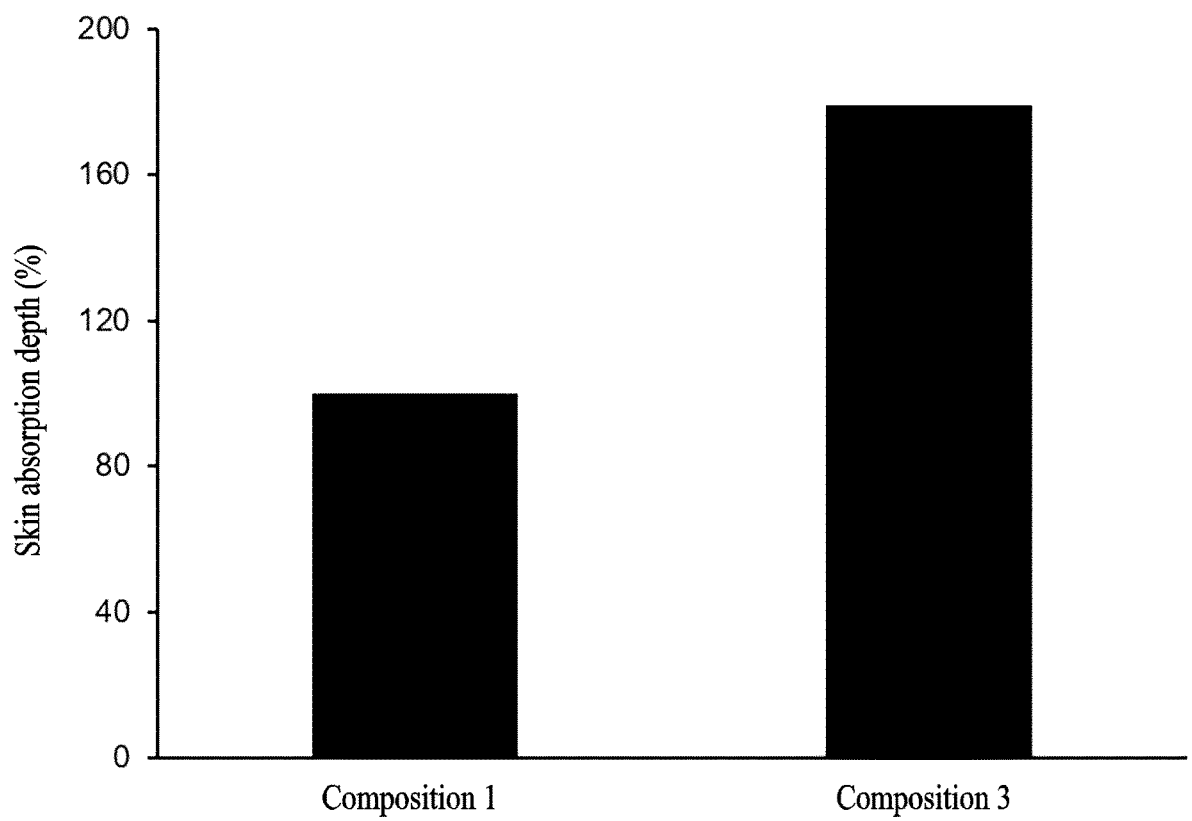
FIG. 13 is a graph comparing the skin absorption depths of the cosmetic composition 3 including the modified spicule of the present disclosure and Cosmetic Composition 1 including a spicule that is not coated with diamond.

✕ Improvement rate (%) = | (after-before) |/before*100
: p < 0.05 by Wilcoxon signed rank test
FF: p < 0.05 by Ranked ANCOVA As a result of measuring skin absorption depths, as shown in Table 6 and FIGS. 12 and 13, when Composition 3 according to the present disclosure was used compared with before using, it was confirmed that the skin absorption depths were 1.791 times and 179% deeper than that of the control group. These results mean that the cosmetic composition according to the present disclosure which is coated with diamond is absorbed into the skin deeper than the control group, which is not, so that the effect is remarkable.

TABLE 6

| (Mean ± SD) | | |
|---|---|---|
| | μm | |
| Classification | Composition 3 | Composition 1 |
| Skin absorption depth | 28.571 ± 12.762 | 15.952 ± 9.698 |
| Ratio (%) of skin absorption depth of Composition 3/Composition 1 | 179.106 | 100.000 |
| Intergroup p-value comparison | Composition 3-Composition 1 | 0.000# |

: p < 0.05 by Wilcoxon signed rank test

Figure 14:
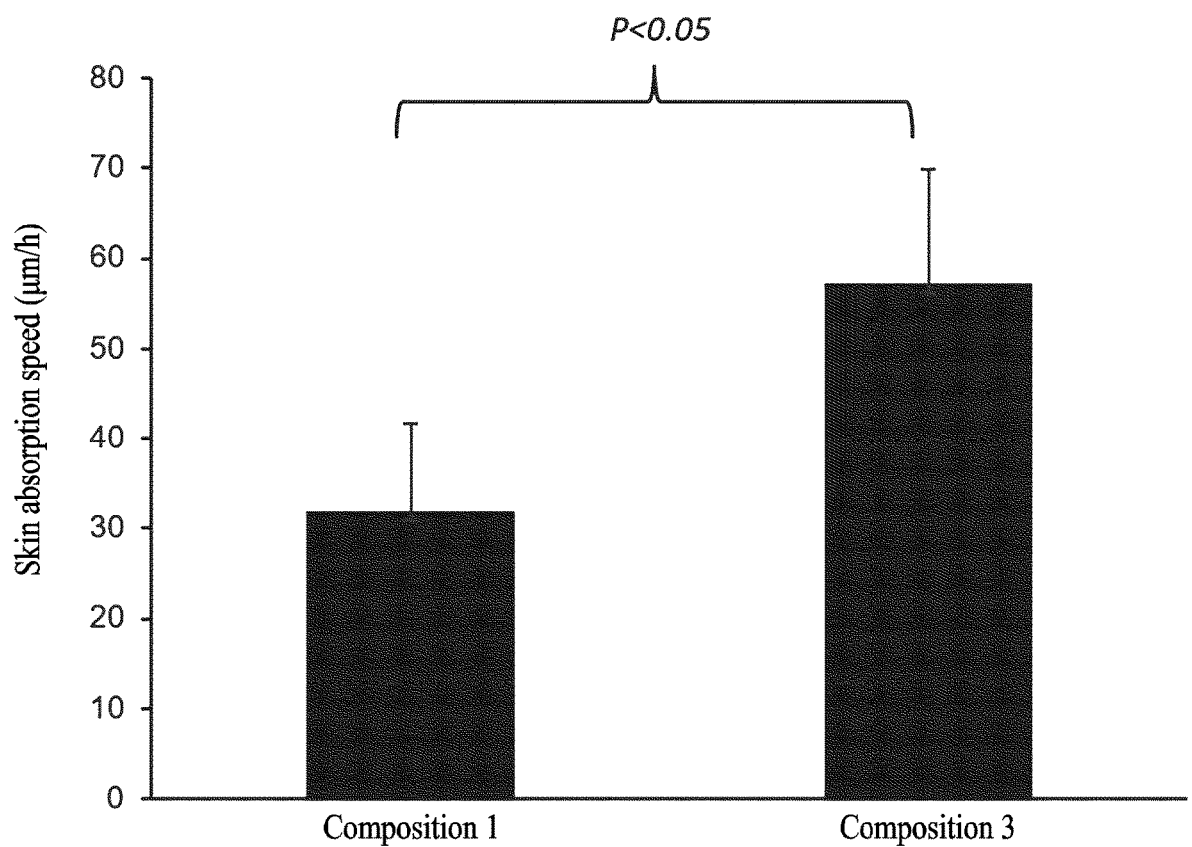
FIG. 14 is a graph showing the skin absorption speeds of the cosmetic composition 3 including the modified spicule of the present disclosure and Cosmetic Composition 1 including a spicule that is not coated with diamond.
Figure 15:
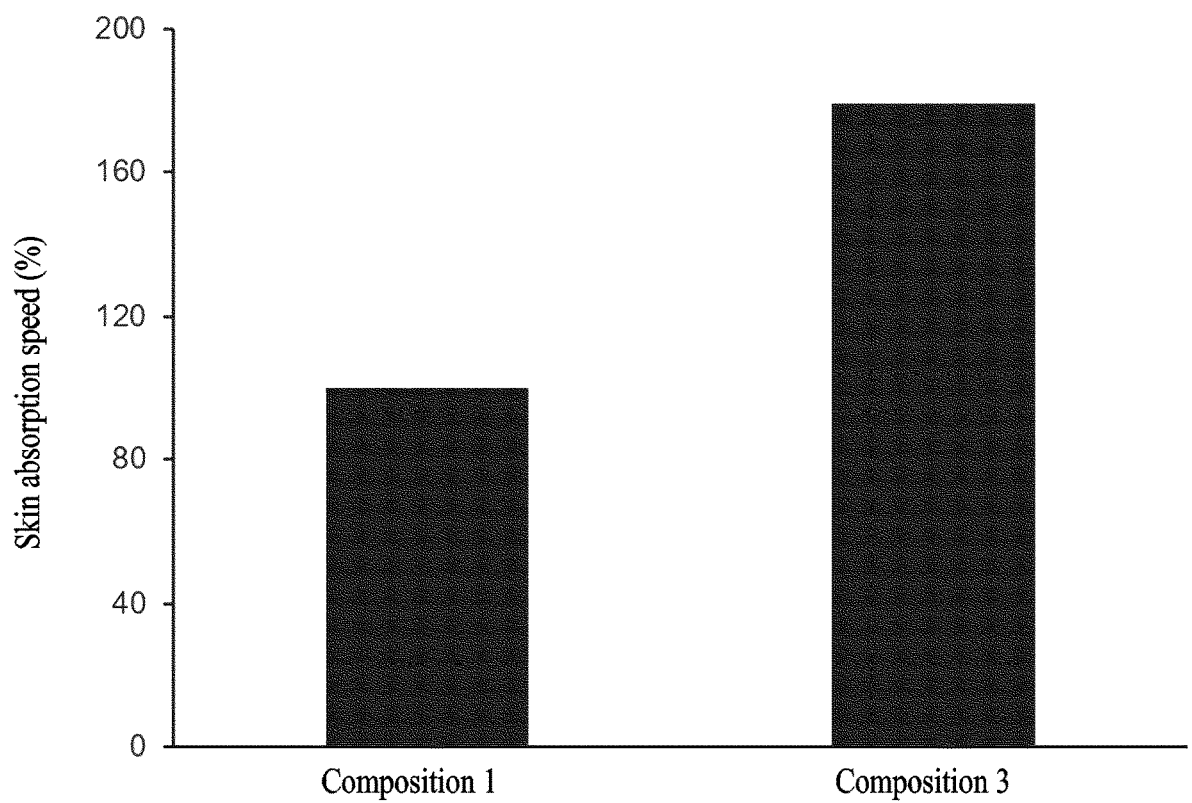
FIG. 15 is a graph comparing the skin absorption speeds of the cosmetic composition 3 including the modified spicule of the present disclosure and Cosmetic Composition 1 including a spicule that is not coated with diamond.

As a result of measuring skin absorption speeds, as shown in Table 7 and FIGS. 14 and 15, when Composition 3 according to the present disclosure was used compared with before using, it was confirmed that the skin absorption speeds were 1.971 times and 179% faster than that of the control group. These results mean that the cosmetic composition according to the present disclosure which is coated with diamond is absorbed into the skin faster than the control group, which is not, so that the effect is remarkable.

TABLE 7

| (Mean ± SD) | | |
|---|---|---|
| | μm/h | |
| Classification | 조성물3 | 조성물1 |
| Skin absorption depth | 57.143 ± 25.523 | 31.905 ± 19.396 |
| Ratio (%) of skin absorption depth of Composition 3/Composition 1 | 179.104 | 100.000 |
| Intergroup p-value comparison | Composition 3-Composition 1 | 0.000# |

: p < 0.05 by Wilcoxon signed rank test 5-4. Validity Survey

After using the test product, test subjects were asked to directly answer the questionnaire with respect to the measurement items in five levels: very good (4), good (3), normal (2), bad (1), and very bad (0). The researcher determined whether there is the efficacy of the test product or not by obtaining the percentage of the number of test subjects for each answer.

As shown in Table 8 below, it was confirmed that the cosmetic composition according to the present disclosure had a high effect of improving the body sensation.

TABLE 8

|  |  | 4* | 3* | 2* | 1* | 0* | Mean | Normal or more |
|---|---|---|---|---|---|---|---|---|
| Improvement of skin absorption degree | Number of people | 7 | 14 | 0 | 0 | 0 | 3.333 | 100.000 |
|  | % | 33.333 | 66.667 | 0.000 | 0.000 | 0.000 |  |  |

*4: Very good, 3: Good, 2: Normal, 1: Bad, 0: Very bad 5-5. Product Preference Survey Evaluation After using the test product, the test subjects were asked to directly answer the questionnaire about the feeling of using the product. The evaluation items were evaluated in five levels of very good (4), good (3), normal (2), bad (1), and very bad (0) for skin moisturization, skin smoothness, spreadability, fragrance, and overall feeling of use.

As shown in Table 9 below, it was confirmed that the preference felt by the test subjects for the cosmetic composition according to the present disclosure was high.

TABLE 9

|  |  | 4* | 3* | 2* | 1* | 0* | Mean | Normal or more |
|---|---|---|---|---|---|---|---|---|
| Skin moisturization | Number of people | 14 | 7 | 0 | 0 | 0 | 3.667 | 100.000 |
|  | % | 66.667 | 33.333 | 0.000 | 0.000 | 0.000 |  |  |
| Skin smoothness | Number of people | 12 | 9 | 0 | 0 | 0 | 3.571 | 100.000 |
|  | % | 57.143 | 42.857 | 0.000 | 0.000 | 0.000 |  |  |
| Spreadability | Number of people | 13 | 8 | 0 | 0 | 0 | 3.619 | 100.000 |
|  | % | 61.905 | 38.095 | 0.000 | 0.000 | 0.000 |  |  |
| Fragrance | Number of people | 9 | 9 | 3 | 0 | 0 | 3.286 | 100.000 |
|  | % | 42.857 | 42.857 | 14.286 | 0.000 | 0.000 |  |  |
| Overall feeling of use | Number of people | 10 | 11 | 0 | 0 | 0 | 3.476 | 100.000 |
|  | % | 47.619 | 52.381 | 0.000 | 0.000 | 0.000 |  |  |

*4: Very good, 3: Good, 2: Normal, 1: Bad, 0: Very bad 5-6. Stability Evaluation and Adverse Reaction Evaluation For the safety of the test product, the incidence rate of adverse reactions was obtained by synthesizing adverse reactions confirmed for all test subjects who used the test product and all adverse reactions reported during the test period, and used as data for product safety evaluation. In addition, for abnormal skin symptoms that occurred during the use of the test product, whether there was an occurrence or not and the symptom level were checked through a questionnaire survey during the test period. As a result, the results of the researcher's visual evaluation of the part using the test product and the results of the test subjects' questionnaires were comprehensively evaluated. Stability evaluation and adverse reaction evaluation were performed.

As a result of the researcher's visual evaluation of the test site during the test period, no specific skin adverse reactions were identified. In addition, as a result of the survey on the test subjects, there were no special reports related to skin adverse reactions, and there were no test subjects either who experienced adverse reactions during the test period.

Although the examples have been described with reference to the limited Examples and drawings as described above, various modifications and variations are possible from the above description by one of ordinary skill in the art. For example, appropriate results can be achieved although described techniques are performed in order different from a described method, and/or described elements are joined or combined in a form different from the described method, or replaced or substituted by other elements or equivalents.

Therefore, other embodiments, other Examples, and equivalents to the claims also belong to the scope of the claims to be described later.

The invention claimed is:

1. A method for manufacturing a spicule coated with ingredients effective for skin improvement and diamond, the method comprising the steps of:
   (a) washing a spicule;
   (b) encapsulating a first active ingredient in inner holes of the washed spicule;
   (c) coating an outside of the spicule in which the first active ingredient is encapsulated in the inner holes with silica;
   (d) coating an amino group onto the spicule by reacting the silica-coated spicule with aminosilane and lysine; and
   (e) coating the amino group-coated silica with a second active ingredient and diamond,
   wherein the first active ingredient and the second active ingredient are each one or more selected from the group consisting of collagen, fish collagen, nano collagen, low molecular weight collagen, vegetable collagen, collagen peptides, amino acids, tripeptides, tetrapeptides, and water-soluble vitamins, and the first active ingredient and the second active ingredient are ingredients that are the same as or different from each other.

2. The method of claim 1, wherein aminosilane of the step (d) is 3-aminopropyltrimethoxysilane.

3. The method of claim 1, wherein lysine of the step (d) is poly-L-lysine.

4. The method of claim 1, wherein aminosilane and lysine of the step (d) have a mixing ratio of 1:1 to 500:1.

5. The method of claim 1, wherein the diamond of the step (e) is one or more selected from the group consisting of microdiamonds, nanodiamonds, and colloidal diamonds.

6. A cosmetic composition comprising the spicule manufactured by the method of claim 1.

7. The cosmetic composition of claim 6, wherein the cosmetic composition has a skin keratin exfoliation effect.

8. The cosmetic composition of claim 6, wherein the cosmetic composition has a wrinkle improvement effect.

\* \* \* \* \*